US00PP18886P2

(12) United States Plant Patent
Smith

(10) Patent No.: US PP18,886 P2
(45) Date of Patent: Jun. 3, 2008

(54) ***CHRYANTHEMUM* PLANT NAMED 'YOBONNIE'**

(50) Latin Name: *Chrysanthemum×morifolium*
Varietal Denomination: Yobonnie

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,396

(22) Filed: Dec. 18, 2006

(51) Int. Cl.
*A01H 5/00* (2006.01)

(52) U.S. Cl. ..... Plt./293

(58) Field of Classification Search ..... Plt./293
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yobonnie', characterized by its compact, upright and outwardly spreading plant habit; freely branching habit; dense and full plant habit; uniform and freely flowering habit; daisy-type inflorescences with elongated oblong to ligulate-shaped ray florets; dark red-colored ray florets; and natural season flowering about September 14$^{th}$ in the Northern Hemisphere.

1 Drawing Sheet

Botanical designation: *Chrysanthemum×morifolium.*
Cultivar denomination: 'Yobonnie'.

BACKGROUND OF THE INVENTION

The present invention relates to a new and distinct cultivar of *Chrysanthemum* plant, botanically known as *Chrysanthemum×morifolium,* commercially grown as a garden *Chrysanthemum* and hereinafter referred to by the name 'Yobonnie'.

The objective of the breeding program is to create new garden type *Chrysanthemum* cultivars having inflorescences with desirable inflorescence forms, attractive floret colors and good garden performance.

The new *Chrysanthemum* originated from a cross-pollination made by the Inventor in March, 2002, in Salinas, Calif. of the *Chrysanthemum×morifolium* cultivar Hot Salsa, disclosed in U.S. Plant Pat. No. 11,918, as the female, or seed, parent with the *Chrysanthemum×morifolium* cultivar Yonatasha, disclosed in U.S. Plant Pat. No. 13,907, as the male, or pollen, parent. The new *Chrysanthemum* was discovered and selected by the Inventor as a single flowering plant within the progeny of the stated cross-pollination in a controlled environment in Alva, Fla. in October, 2002.

Asexual reproduction of the new *Chrysanthemum* by vegetative cuttings was first conducted in Alva, Fla. in January, 2003. Asexual reproduction by cuttings has shown that the unique features of this new Chrysanthemum are stable and reproduced true to type in successive generations.

SUMMARY OF THE INVENTION

Plants of the cultivar Yobonnie have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yobonnie'. These characteristics in combination distinguish 'Yobonnie' as a new and distinct garden *Chrysanthemum* cultivar:

1. Compact, upright and outwardly spreading plant habit.
2. Freely branching habit; dense and full plant habit.
3. Uniform and freely flowering habit.
4. Daisy-type inflorescences with elongated oblong to ligulate-shaped ray florets.
5. Dark red-colored ray florets.
6. Natural season flowering about September 14$^{th}$ in the Northern Hemisphere.

In side-by-side comparisons conducted in Alva, Fla., plants of the new *Chrysanthemum* differed from plants of the female parent, the cultivar Hot Salsa, in the following characteristics:

1. Plants of the new *Chrysanthemum* were shorter and more mounded than plants of the cultivar Hot Salsa.
2. Plants of the new *Chrysanthemum* flowered more uniformly than plants of the cultivar Hot Salsa.
3. Ray florets of plants of the new *Chrysanthemum* were darker red in color than ray florets of plants of the cultivar Hot Salsa.

In side-by-side comparisons conducted in Alva, Fla., plants of the new *Chrysanthemum* differed from plants of the male parent, the cultivar Yonatasha, in the following characteristics:

1. Plants of the new *Chrysanthemum* were not as spherical in shape as plants of the cultivar Yonatasha.
2. Plants of the new *Chrysanthemum* flowered earlier then plants of the cultivar Yonatasha when grown under natural season conditions.
3. Plants of the new *Chrysanthemum* and the cultivar Yonatasha differed in ray floret color as plants of the cultivar Yonatasha had light purple-colored ray florets.

Plants of the new *Chrysanthemum* can be compared to plants of the *Chrysanthemum* cultivar Foxy Yonatasha, disclosed in U.S. Plant Pat. No. 15,351. In side-by-side comparisons conducted in Alva, Fla., plants of the new

*Chrysanthemum* differed from plants of the cultivar Foxy Yonatasha in the following characteristics:

1. Plants of the new *Chrysanthemum* were not as spherical in shape as plants of the cultivar Foxy Yonatasha.
2. Plants of the new *Chrysanthemum* flowered earlier than plants of the cultivar Foxy Yonatasha.
3. Ray florets of plants of the new *Chrysanthemum* were darker red in color than and did not fade as quickly as ray florets of plants of the cultivar Foxy Yontasha.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Yobonnie'.

The photograph at the top of the sheet is a close-up view of typical inflorescences of 'Yobonnie'.

DETAILED BOTANICAL DESCRIPTION

The aforementioned photographs and following observations and measurements describe plants grown in Fletcher, N.C. during the summer in an outdoor nursery and under conditions and practices which approximate those generally used in commercial garden *Chrysanthemum* production. During the production of the plants, day temperatures averaged 29° C. and night temperatures averaged 16° C. Plants were grown in 15-containers, exposed to long day/short night conditions and pinched about two weeks later. About two weeks after the pinch, the photoinductive short day/long night treatments were started. Plants used in the photographs and for the description were about three months old. In the following description, color references are made to The Royal Horticultural Society Colour Chart, 1995 Edition, except where general terms of ordinary dictionary significance are used.

Botanical classification: *Chrysanthemum×morifolium* cultivar Yobonnie.

Parentage:

*Female, or seed, parent.*—*Chrysanthemum×morifolium* cultivar Hot Salsa, disclosed in U.S. Plant Pat. No. 11,918.

*Male, or pollen, parent.*—*Chrysanthemum×morifolium* cultivar Yonatasha, disclosed in U.S. Plant Pat. No. 13,907.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Herbaceous daisy-type garden *Chrysanthemum*. Stems upright and outwardly spreading giving a uniformly mounded appearance to the plant. Freely branching habit, about five to six lateral branches develop after removal of terminal apex (pinching) each with numerous secondary laterals; dense and full plant habit. Strong and vigorous growth habit.

*Plant height.*—About 21 cm.

*Plant width.*—About 29 cm.

*Lateral branches.*—Length: About 18 cm. Diameter: About 5 mm. Internode length: About 1.6 cm. Strength: Strong. Texture: Pubescent. Color: 148A.

*Leaves.*—Arrangement: Alternate, simple. Length: About 5.5 cm. Width: About 4.4 cm. Apex: Broadly acute. Base: Attenuate. Margin: Palmately lobed, sinuses between lateral lobes mostly parallel. Texture, upper and lower surfaces: Fine pubescence; veins prominent on lower surface. Color: Developing and fully expanded foliage, upper surface: 147A; venation, 147B. Developing and fully expanded foliage, lower surface: 147B; venation, 147B. Petiole: Length: About 1.4 cm. Diameter: About 2.5 mm. Texture, upper and lower surfaces: Pubescent. Color, upper surface: 147A. Color, lower surface: 147B.

Inflorescence description:

*Appearance.*—Daisy-type inflorescence form with elongated oblong to ligulate-shaped ray florets. Inflorescences borne on terminals above foliage. Disk and ray florets arranged acropetally on a capitulum. Inflorescences faintly fragrant.

*Flowering response.*—Under natural season conditions, plants flower about September 14$^{th}$ in the Northern Hemisphere. At other times of the year, inflorescence initiation and development can be induced under short day/long night conditions (at least 13.5 hours of darkness). Early flowering habit; plants exposed to photoinductive short day/long night conditions flower about 52 days later.

*Postproduction longevity.*—Inflorescences maintain good color and substance for about three weeks in an outdoor nursery.

*Quantity of inflorescences.*—About 41 inflorescences develop per lateral branch.

*Inflorescence bud.*—Height: About 1.1 cm. Diameter: About 1 cm. Shape: Ovoid. Color: 182B.

*Inflorescence size.*—Diameter: About 4 cm. Depth (height): About 1.8 cm. Disc diameter: About 6 mm. Receptacle diameter: About 1.3 cm. Receptacle height: About 4 mm.

*Ray florets.*—Shape: Elongated-oblong to ligulate. Orientation: Initially upright, then about 90° from vertical or perpendicular to peduncle. Aspect: Initially incurved, then mostly flat with development. Length: About 1.8 cm. Width: About 5 mm. Apex: Emarginate. Base: Acute. Margin: Entire. Texture, upper and lower surfaces: Smooth, glabrous, satiny. Number of ray florets per inflorescence: About 42 arranged in about five whorls. Color: When opening, upper surface: Slightly darker than 46A. When opening, lower surface: 182C to 182D. Fully opened, upper surface: 46A; with development, color becomes closer to 185B to 185C. Fully opened, lower surface: 182B; color becoming closer to 56A with development.

*Disc florets.*—Shape: Tubular, elongated. Length: About 5 mm. Diameter: About 1.5 mm. Number of disc florets per inflorescence: About 66. Color, immature: Apex: Close to 1B. Mid-section: Close to 145D. Base: Close to 157A. Color, mature: Apex: Close to 12A. Mid-section: Close to 12C. Base: Close to 145D.

*Phyllaries.*—Number of phyllaries per inflorescence: About 18 arranged in about three whorls. Length: About 7 mm. Width: About 3 mm. Shape: Elliptical. Apex: Acute. Base: Truncate. Texture, upper surface: Smooth, waxy. Texture, lower surface: Pubescent. Color, upper surface: Close to 147A. Color, lower surface: Close to 148A.

*Peduncles.*—Length: About 4.3 cm. Diameter: About 1.5 mm. Angle: About 45° from vertical. Strength: Strong. Texture: Pubescent; longitudinally ridged. Color: Close to 148B.

*Reproductive organs.*—Adroecium: Stamen number: About five per floret. Filament length: About 1 mm. Filament color: Close to 1A. Anther length: About 1 mm. Anther shape: Oblong. Anther color: Close to 4A. Pollen amount: None observed. Gynoecium: Pistil length: About 4 mm. Stigma shape: Bi-parted. Stigma color: Close to 2C. Style length: About 3 mm. Style color: Close to 145D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and to tolerate temperatures from about 0° C. to about 38° C.

It is claimed:

1. A new and distinct *Chrysanthemum* plant named 'Yobonnie' as illustrated and described.

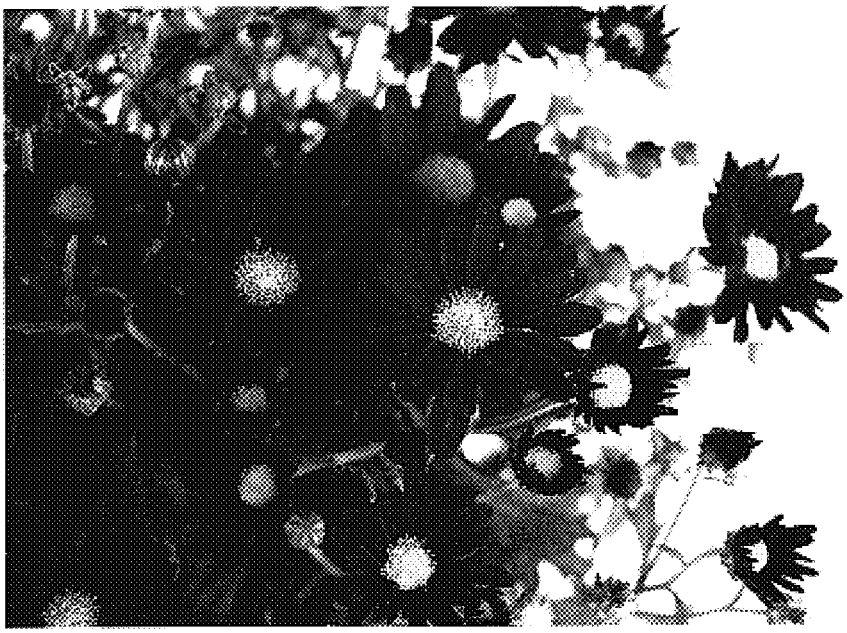
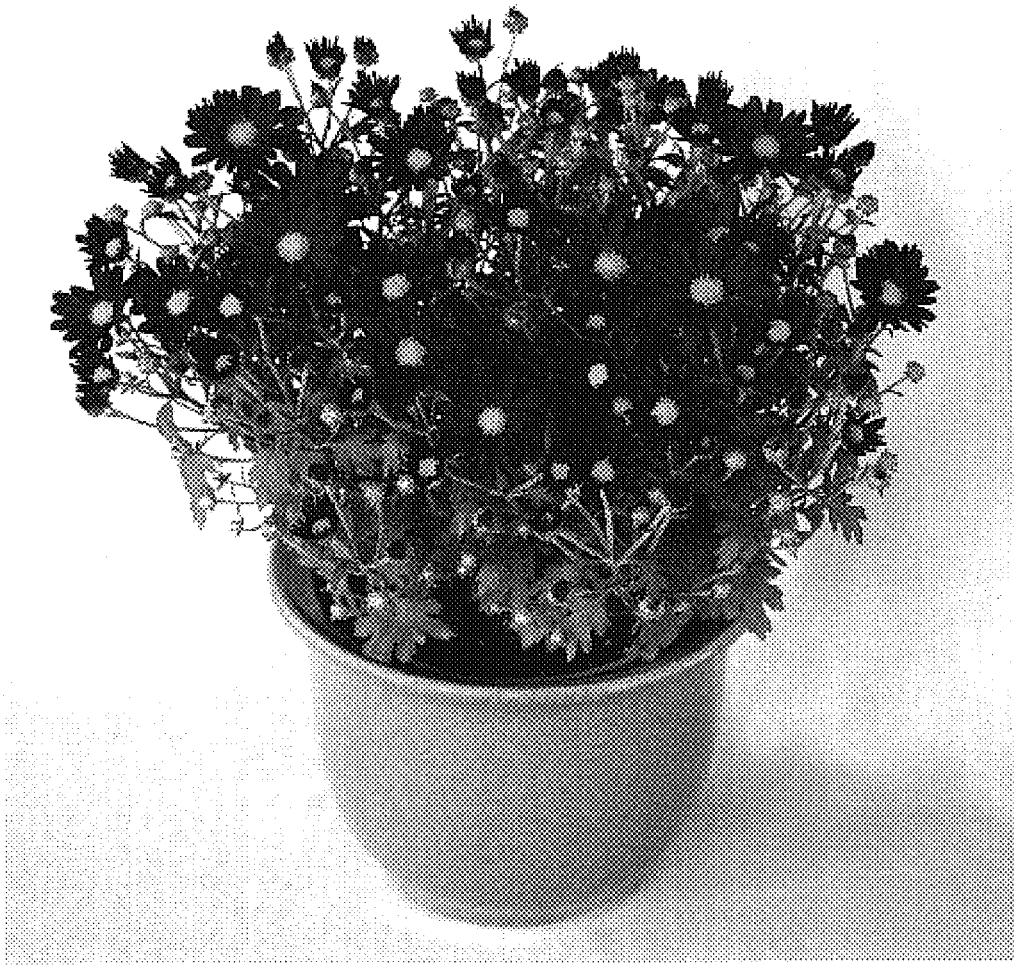

* * * * *